United States Patent [19]

McKenna

[11] Patent Number: 4,777,963
[45] Date of Patent: Oct. 18, 1988

[54] RESPIRATION MONITOR

[76] Inventor: Kevin McKenna, 58 W. Gradwell Ave., Maple Shade, N.J. 08052

[21] Appl. No.: 63,448

[22] Filed: Jun. 18, 1987

[51] Int. Cl.⁴ ............................................. A61B 5/08
[52] U.S. Cl. .................................... 128/724; 128/640
[58] Field of Search ............... 128/639, 640, 716, 718, 128/719, 724

[56] References Cited

U.S. PATENT DOCUMENTS

| | | | |
|---|---|---|---|
| 2,943,628 | 7/1960 | Howell | 128/640 |
| 3,232,288 | 2/1966 | Krobath | 128/724 |
| 3,241,549 | 3/1966 | Tyler | 128/724 |
| 3,935,742 | 2/1976 | Rybak | 128/716 |

FOREIGN PATENT DOCUMENTS 2575917  7/1986  France .................... 128/724

OTHER PUBLICATIONS

Nasa Tech. Brief, by Long et al., "Nosepiece Respiration Monitor", Dec. 1968.

Primary Examiner—Edward M. Coven
Assistant Examiner—Randy Citrin
Attorney, Agent, or Firm—Norman E. Lehrer

[57] ABSTRACT

A respiration monitoring device for an infant patient includes three thermistors which are arranged so that one thermistor underlies each nostril and one thermistor overlies the patient's mouth. The thermistors are mounted on a thin flexible support member having an adhesive back so that the same can be temporarily secured to the patient's nose. The support member includes an upper portion which overlies the bridge of the nose and a lower portion which overlies the nostrils. The lower portion has a pair of openings therein and two of the thermistors are arranged in these openings. Each thermistor is enclosed in a fabric mesh material to prevent inhalation of fragments in the event of breakage. The support member may also carry a $CO_2$ sensor, an oxygen saturation sensor and/or a pulse rate sensor.

5 Claims, 1 Drawing Sheet

RESPIRATION MONITOR

BACKGROUND OF THE INVENTION

The present invention is directed toward a respiration monitoring device and more particularly toward such a device which is utilized to monitor an infant's breathing while the patient is sleeping.

Infant apnea syndrome, the new name for near-miss SIDS, characterizes infants between 42 weeks gestational age and 12 months chronological age who experience clinically significant apneas having a duration of 10 seconds or more. Documentation of this phenomenon is generally obtained during polysomnographic recording sessions while the subject sleeps. During cardio-respiratory assessment, a major difficulty is the inability to track airflow continuously and reliably over prolonged periods of time.

Heat resistant thermistors are widely used to detect airflow from the nose and mouth and function by sensing ambient temperature changes proximal to them. Thermistors are more advantageous than other devices for qualitative airflow analysis because of their small size and rapid responsiveness. However, difficulties have been experienced, particularly with infants, in maintaining the thermistors in their proper position.

Several devices have been proposed in the past which are intended to be worn by a subject in order to position the thermistors. Examples of these are shown in U.S. Pat. Nos. 2,831,181; 3,232,288 and 3,241,549. These devices, however, are intended primarily for adult subjects and do not readily lend themselves to use with sleeping infants. The writhing and other movements of the infant during sleep tend to dislodge these devices and can also create artifacts and false readings.

In order to overcome the problems of the prior art devices which include harnesses or straps or the like for holding the thermistors in place, some investigators have attempted to simply tape the thermistors in place in order to detect nasal and oral airflow. Using this technique, however, it is difficult to properly align the various thermistors. Furthermore, even if an investigator succeeds in properly placing the thermistors, this is a time-consuming procedure which can be annoying to the infant. Even further, it is difficult to accurately reproduce the positions of the thermistors from day to day for a series of tests.

SUMMARY OF THE INVENTION

The present invention overcomes the deficiencies of the prior art described above. The respiration monitoring device of the invention is specifically designed for use with an infant patient and includes three thermistors which are arranged so that one thermistor underlies each nostril and one thermistor overlies the patient's mouth. The thermistors are mounted on a thin flexible support member having an adhesive back so that the same can be temporarily secured to the patient's nose. The support member includes an upper portion which overlies the bridge of the nose and a lower portion which overlies the nostrils. The lower portion has a pair of openings therein and two of the thermistors are arranged in these openings. Each thermistor is enclosed is a fabric mesh material to prevent inhalation of fragments in the event of breakage. The support member may also carry a $CO_2$ sensor, an oxygen saturation sensor and/or a pulse rate sensor.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
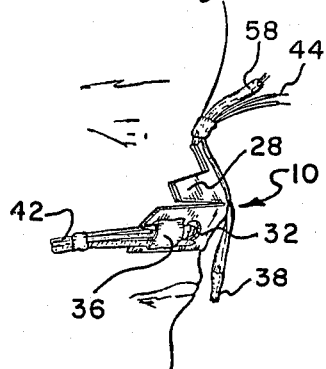
FIG. 1 is a side view of a respiration monitoring device constructed in accordance with the principles of the present invention and shown in use with an infant patient.
Figure 2:
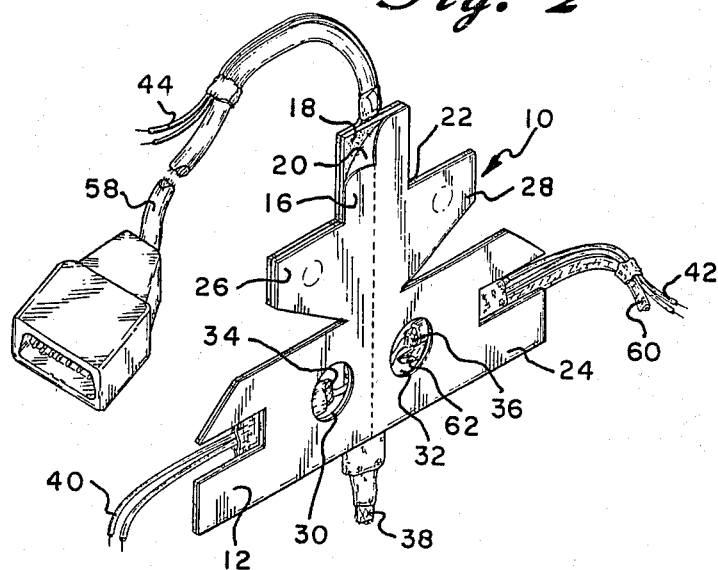
FIG. 2 is a perspective view of the underside of a respiration monitoring device prior to its use.
Figure 3:
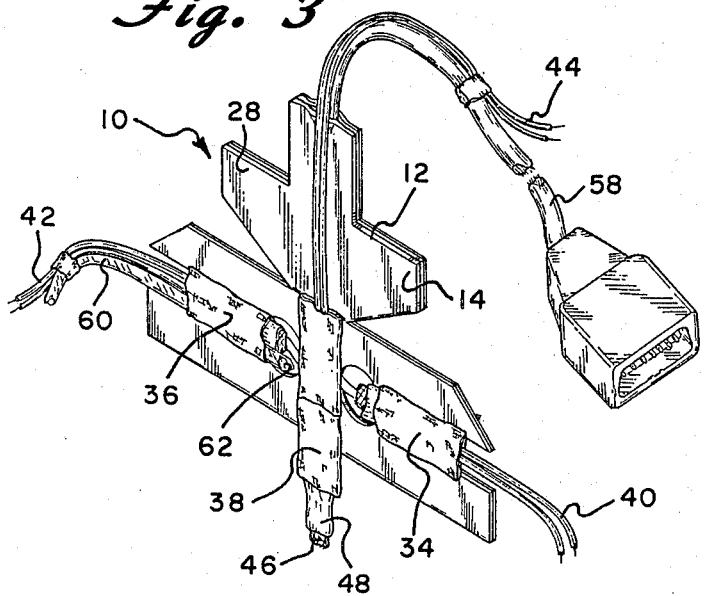
FIG. 3 is a view similar to FIG. 2 showing the upper side of the device.

Referring now to the drawings in detail wherein like reference numerals have been used throughout the various figures to designate like elements, there is shown in Figures 1, 2 and 3 a respiration monitoring device constructed in accordance with the principles of the present invention and designated generally as 10. The device 10 is comprised of a substantially thin, flexible support member 12 which is preferably made from a microfoam tape. The support member has an outer surface 14 and an inner surface 16. An adhesive 18 coats substantially the entire inner surface and is capable of temporarily but firmly securing the support member 12 to a patient's skin. A removable release paper 20 covers the adhesive 18 and protects the same until the device is ready to be used. At that time, the paper 20 is peeled off to thereby expose the adhesive.

The support member is formed into a substantially inverted T-shape having an upper portion 22 and a lower portion 24. As shown most clearly in FIG. 1, the upper portion 22 with its side wings 26 and 28 is adapted to overlie the bridge of a patient's nose when the same is in place. The lower portion 24 of the support member is adapted to overlie the patient's nostrils.

A pair of spaced openings 30 and 32 are formed in the lower portion 24 of the support member 12. These openings are adapted to be in substantial alignment with the patient's nostrils when the device is in place as shown in FIG. 1. A pair of negative temperature coefficient thermistors 34 and 36 are carried by the lower portion 24 of the support member and are arranged so that the operative elements thereof are exposed through the openings 30 and 32, respectively. Thus, when the device 10 is in place on a patient's nose, the thermistors 34 and 36 are substantially aligned beneath the patient's nostrils.

A third thermistor 38 is also carried by the support member 12 and extends downwardly below the lower portion 24. As shown most clearly in FIG. 1, the thermistor 38 directly overlies the patient's mouth when the device is in place on the patient's nose. Each of the thermistors 34, 36 and 38 is provided with lead wires 40, 42 and 44, respectively, which connects the same to the monitoring equipment.

Figure 5:
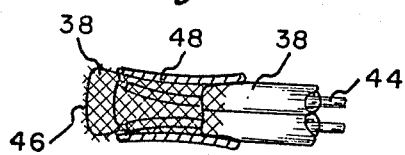
FIG. 5 is a detailed view of a thermistor utilized with the present invention.

It is known that thermistors of the type utilized with the present invention are brittle and can be broken in use. Means are, therefore, provided for preventing inhalation of the broken pieces. As shown in FIG. 5, each thermistor such as thermistor 38 is covered by a nylon mesh material 46. The mesh is held in place by the use of an elastic sleeve 48. It will be understood that the thermistors 34 and 36 are similarly protected by a nylon mesh. Each of the thermistors along with its nylon mesh protector and sleeve is secured to the outer surface of the support member through the use of sutures or substantially any other fastening means.

Figure 4:
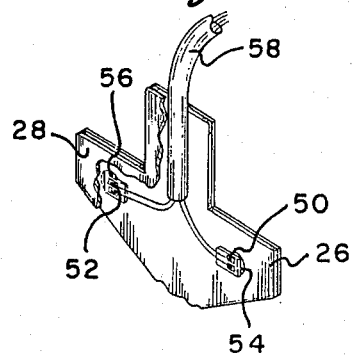
FIG. 4 is a perspective view with a portion broken away showing the details of the upper part of the device shown in FIG. 3.

So that the device 10 can also be used for sensing oxygen saturation and pulse rate, the device is also provided with an oxygen saturation sensor 50 and a pulse rate sensor 52. As shown most clearly in FIG. 4, these sensors 50 and 52 are preferably embedded within the support member 12 in the side wings 26 and 28, respectively, of the upper portion 22. The sensors 50 and 52 may be exposed through the openings 54 and 56 so as to come into contact with the patient's skin when the device is in place. Appropriate lead wires 58 connect the sensors 50 and 52 to the monitoring equipment.

The device 10 is also equipped with a means for sensing carbon dioxide. To this end, the device is provided with a carbon dioxide sensing tube 60. The end 62 of the tube 60 is exposed through the opening 32 and lies adjacent the end of the thermistor 36. This allows the carbon dioxide being exhaled by the patient to be monitored.

The device of the present invention is utilized in the following manner. First, the paper backing 20 is removed from the adhesive 18 on the lower surface of the support member 12. The upper portion 22 of the support member is then centered over the bridge of the patient's nose with the wings 26 and 28 then being pressed against the sides of the nose. As is known in the art, the adhesiveness of the support member 12 can be enhanced by the use of tincture of benzoin. The lower portion 24 of the support member 12 is then folded upwardly until the same comes into contact with the area of the nose surrounding the nostrils. This results in a significant amount of skin contact thereby maintaining the device securely in place. With the device in place as shown in FIG. 1, the thermistors 34 and 36 are substantially aligned beneath the patient's nostrils and the thermistor 38 overlies the patient's mouth so that airflow can be detected from the nose and the mouth. At the same time, carbon dioxide can be sensed through the use of the tube 60 and oxygen saturation and pulse rate can be sensed through the use of sensors 50 and 52.

The present invention may be embodied in other specific forms without departing from the spirit or essential attributes thereof and accordingly reference should be made to the appended claims rather than to the foregoing specification as indicating the scope of the invention.

I claim:

1. A respiration monitoring device comprising:
   a substantially thin, flexible support member having an outer surface and an inner surface;
   an adhesive carried by said inner surface, said adhesive being capable of temporarily but firmly securing said support member to a patient's skin;
   said support member having an upper portion which is adapted to overlie the bridge of a patient's nose when the same is in place and a lower portion which is adapted to overlie the patient's nostrils;
   a pair of spaced openings in the lower portion of said support member, said openings being adapted to be in substantial alignment with the patient's nostrils when said device is in place;
   a pair of thermistors carried by said support member, each thermistor being located in a different one of said openings whereby, when said device is in place on a patient's nose, said thermistors are substantially aligned beneath the patient's nostrils and, each of said thermistors being separately enclosed in a fabric mesh material to prevent pieces of the thermistor from being inhaled in the event of breakage of the same.

2. The invention as claimed in claim 1 further including a third thermistor carried by said support member and extending downwardly therefrom, said third thermistor being adapted to overlie a patient's mouth when said device is in place on the patient's nose.

3. The invention as claimed in claim 1 wherein said support member further carries a carbon dioxide sensing tube, an end of said tube lying within one of said openings.

4. The invention as claimed in claim 1 further including an oxygen saturation sensor carried by said support member.

5. The invention as claimed in claim 1 further including a pulse rate sensor carried by said support member.

* * * * *